United States Patent [19]
Cincotta et al.

[11] Patent Number: 5,952,329
[45] Date of Patent: Sep. 14, 1999

[54] BENZOPHENOTHIAZINE AND BENZOPORPHYRIN DYE COMBINATION PHOTODYNAMIC THERAPY OF TUMORS

[75] Inventors: Anthony H. Cincotta, Charlestown; Louis Cincotta, Andover; Tayyaba Hasan, Arlington, all of Mass.

[73] Assignees: The General Hospital Corporation, Boston; Rowland Institute for Science, Cambridge, both of Mass.

[21] Appl. No.: 08/787,665

[22] Filed: Jan. 23, 1997

Related U.S. Application Data

[60] Provisional application No. 60/010,485, Jan. 23, 1996.

[51] Int. Cl.$^6$ .......................... A61K 31/54; A61K 31/40
[52] U.S. Cl. ......................................... 514/224.5; 514/410
[58] Field of Search ................................. 514/224.5, 410

[56] References Cited

U.S. PATENT DOCUMENTS 4,920,143  4/1990  Levy et al. ............................. 514/510

OTHER PUBLICATIONS

Louis Cincotta, *A novel Benzophenothiazine Photodynamic Therapy Agent*, Special Radiation Biology Seminar, Roswell Park Cancer Institute (May 23, 1994).
*PDT Expanding the Database*, International Photodynamics, pp. 2–3 (Mar. 1995).
L. Cincotta, et al., *Photochemistry and Photobiology*, Abstract TMP–E5, p. 67S (May 1995).
P.G. Johnson, et al., *Photochemistry and Photobiology*, Abstract TMP–E11, p. 69S (May 1993).
P.G. Johnson, et al., *Photochemistry and Photobiology*, Abstract MAM–E5, p. 50S (May 1993).
J.S. Nelson, *JNCI* 82:868–873 (Jan. 1990).
P.G. Johnson, *22nd Annual Mtg. Am. Soc. Photobiology*, Abstract MAM–F6, p. 47S (1994).
Foultier, M.T. et al., *J. Photochem. Photobiol. B. Biol.*, 10:119–132 (1991).
A.H. Cincotta et al., *Chemical Abstracts*, 119:90259, 1993.
J.W. Foley et al., *Chemical Abstracts*, 115:202119, 1991.
C.W. Lin et al., *Chemical Abstracts*, 115;445240, 1990.
Anna M. Richter, et al., Preliminary Studies on a More Effective Phototoxic Agent Than Hematoporphyrin, JNCI vol. 79, No. 6, pp. 1327–1332 (Dec. 1987).
Anna Richter, et al., Characterization of Benzoporphyrin Derivative, a new Photosensitizer, Proc. SPIE Advances in Photochemotharapy, pp. 132–138, vol. 997 (1988).
Louis Cincotta, et al.,Novel Phenothiazinium Photosensitizers For Photodynamic Therapy, Proc. SPIE 997:145–153 (Sep. 6–7, 1988).
J. Stuart Nelson et al., Use of Multiple Photosensitizers and Wavelengths During Photodynamic Therapy: A New Approach to Enhance Tumor Eradication, JNCI, 82:863–873 (1990).
Anthony H. Cincotta, et al., Photodynamic Therapy: Mechanisms II, Progress in Biomedical Optics, SPIE vol. 1203, pp. 202–210 (1990).
Joerg G. Moser, et al., Photodynamic Cancer Therapy: Fluorescence Localization and Light Absorption Spectra of Chlorophyll–Derived Photosensitizers Inside Cancer Cells, Optical Engineering, 31:(7), 1441–1446 (Jul. 1992).
International Preliminary Examination Report dated Nov. 5, 1997 received in the corresponding international application.

*Primary Examiner*—Zohreh Fay
*Attorney, Agent, or Firm*—Darby & Darby

[57] ABSTRACT

A method of ablating the growth of or eradicating neoplasms in mammals by (a) contacting the cells of the neoplasm with an effective amount of a combination of photoactive chromophores, and (b) exposing the chromophore-contacted neoplastic cells to light with a wavelength or wavelengths predetermined to be absorbed by the chromophores, the light also having a predetermined power density and energy level.

18 Claims, 6 Drawing Sheets

BPD-MA

EtNBS

BENZOPHENOTHIAZINE AND BENZOPORPHYRIN DYE COMBINATION PHOTODYNAMIC THERAPY OF TUMORS

This application claims priority pursuant to 35 U.S.C. §119 from U.S. Provisional Application Ser. No. 010,485 filed Jan. 23, 1996, the disclosure of which is incorporated herein in its entirety by reference.

This invention was made with government support under contract N00014-94-I-0927 awarded by the Department of the Navy. The government has certain rights in the invention.

BACKGROUND OF THE INVENTION

Photodynamic therapy (PDT) involves the systemic administration of a tumor localizing photosensitizing drug that is relatively benign in the absence of light. However, photoactivation of the sensitizer in the presence of oxygen generates highly reactive and cytotoxic molecular species through various photophysical pathways (i.e. Type I or Type II mechanisms) which have the ability to destroy malignant tissue (Kessel, D. *Photochem. Photobiol.* 39:851–859, 1984; Foote, C. S. *Science* 162:963–970; Gomer, C. J. *Photochem. Photobiol.* 54:1093–1107; Moan, J. et al., *Photochem. Photobiol.* 55:931–948, 1992). Since tissue injury requires the simultaneous presence of both photosensitizer and light, spatial confinement of the photoirradiation to the proximity of the tumor imparts a dual selectivity to the treatment. This enhanced selectivity results in a modality of cancer treatment with minimal side effects and thus represents a major advantage over the more common therapeutic approaches (surgery, chemotherapy and ionizing radiation therapy) in use today. Currently, world wide clinical investigations of PDT are being carried out with Photofrin™ and HPD. Photofrin™ has recently been approved for use by health agencies in Canada (prophylaxis of recurrent papillary bladder tumors), the Netherlands (early and late stage lung cancer and for obstructing esophageal tumors) and Japan (early stage lung, esophagus, bladder, gastric and cervical cancers). Although encouraging results have been obtained with these photosensitizing agents for a wide variety of tumors, it appears that the following limitations may adversely affect the therapeutic outcome of PDT: (a) a low absorption coefficient in the region where activating light penetrates tissue most efficiently (600–900 nm) limits the depth of PDT damage in large tumors; (b) acute effects leading to rapid vascular occlusion and subsequent loss of oxygen supply are primarily responsible for tumor eradication, not direct tumor cell killing; because photodynamic processes are dependent on oxygen, this rapid shift of cells into hypoxia may limit the further photodestruction of a fraction of the tumor cells (Henderson, B. W. et al., *Photochem. Photbiol.* 49:299–304, 1989; Tromberg, B. J. et al., *Photochem. Photobiol.* 52:375–385, 1990) and (c) prolonged retention of these drugs in the skin leads to dermal photosensitivity for months following treatment.

The successes of PDT has fostered the search for and development of "second generation" photocytotoxic compounds in the hopes of increasing the efficacy of the treatment and minimizing the limitations displayed by the drugs currently in use. The in vitro and in vivo use of PDT employing 5-ethylamino-9-diethylaminobenzo[a]phenothiazinium chloride (EtNBS) have been under investigation (Cincotta, L. et al., *Photochem. Photobiol.* 46:751–758, 1987; Cincotta, A. H. et al., *SPIE Proceedings* 1203:202–210, 1990; Cincotta, L., et al., *Cancer Res.* 53:2571–2580, 1993; Cincotta, L., *Cancer Res.* 54:1249–1258, 1994). This novel photosensitizer possesses several characteristics which differentiate it from the porphyrin family of drugs (including Photofrin™ and HPD), the largest class of photosensitizers investigated for PDT. First, EtNBS is easily synthesized as a single, pure compound. Second, the rapid intracellular accumulation of EtNBS leads to tumor destruction primarily through direct cell killing with minimal effects to the vasculature. Third, it absorbs light (652 nm) very efficiently (extinction coefficient 20×Photofrin™) in the "therapeutic window". Fourth, the drug is essentially eliminated from the majority of murine tissues 24 hours after its administration and importantly, insignificant damage occurs to the surrounding normal skin following PDT of subcutaneous tumors.

Benzophorphyrin derivative mono-acid A ring (BPD-MA), disclosed in Levy et al., U.S. Pat. No. 4,920,143 has also shown promise in studies on photodynamic therapy of tumors, it being reported that BPD-MA is a more effective phototoxic agent than hematoporphyrin (HPD) (Richter, A. M. et al., *JNCI* 79:1327–1332, 1987).

In order to further increase the selectivity and/or efficacy of cancer treatments, approaches using various combinations of surgery, radiotherapy, chemotherapy, hyperthermia, and more recently immunotherapy are becoming more prevalent. These other therapies have been investigated in conjunction with PDT in order to enhance tumor eradication and PDT has been successfully combined with many of these other therapies. There have, however, been only a limited number of studies in which researchers used a combination of photosensitizers in order to achieve enhanced PDT effects. The choice of drugs in these studies was usually based on an attempt to exploit differences in the photosensitizers' mechanism(s) of action or cellular site(s) of toxicity. Nelson et al., *JNCI* 82:868–873, (1990) studied the combination of Photofrin II and meso-tetra-(4-sulfonatophenyl)-porphine) (TPPS4), which typically acts by direct cell killing, with the EMT-6 tumor model. In this study the treated tumors were 5–7 mm in diameter; larger tumors gave unsatisfactory results, i.e. they did not respond significantly to treatment.

Nelson et al. found that the effects observed were not the result of two different mechanisms of action (vasculature shut down and direct intracellular effects) but solely the result of damage to the microvasculature by both compounds.

Johnson et al., *Abst. 21st Ann. Mtng. Am. Soc. Photobiol.* MAM-F6, 47S–48S, (1994), examined the effects resulting from the combination of an anionic and cationic photosensitizer, hexyl pyropheophorbide hexyl ether and Victoria Blue-BO, respectively, on Colon 26 tumors. Their data implies that PDT with the dual photosensitizers gave an enhanced response and also that the combined response was the result of each drug eliciting a different photoeffect. When applied to relatively small tumors (30–40 mm$^3$), this combination phototherapy resulted in a cure rate of 23%.

Foultier et al., *J. Photochem. Photobiol. B. Biol.* 10:119–132, (1991), investigated the multidrug treatment of L1210 leukaemic cells using two photosensitizers, hematoporphyrin derivative and rhodamine 123, that localize to different parts of cells. The combination therapy did not increase cell toxicity except at high drug doses.

The method of the instant invention differs from the above mentioned combination PDT protocols in several important ways. For example, the tumors which can be successfully treated in mouse tumor models by the present invention are large (8–10 mm) compared to the tumors (5–7 mm) usually treated in the PDT literature, and yet 76% were eradicated. Large tumors have a history of poor response to PDT; as a result, the majority of the prior investigations using either EtNBS or BPD-MA have been carried out on tumors less than 7 mm in diameter. Previous studies by the present inventors have shown that large tumors initially respond to EtNBS-PDT (eschar formation, suppression of growth) but they match the control tumor weights at 2 weeks post-PDT. The relationship between tumor volume and response to HPD-PDT using the RIF (radiation induced fibrosarcoma) animal model has also shown a direct correlation between tumor size and rate of regrowth (Al-Watban, A. H. F., *Surgery and Medicine* 10:165–172, 1990). It is accepted by the art that the incomplete tumor destruction observed when treating large tumors results from an inadequate penetration of the tumor by the activating light source.

Another difference between the method of the present invention and prior art methods are the unexpected and surprising results achievable by the invention. Histological examination of the EtNBS/BPD-MA treated tumors 24 h post PDT showed virtually no damage to the vasculature, as evidenced by little if any extravasation of red blood cells, no stasis, no damage to the surrounding normal tissue (skin), but nearly total damage to the tumor mass (cells were highly pyknotic). There was also a substantial decrease in the total tumor cell density following PDT. The fact that the 24 h histology showed no visible damage to the tumor vasculature was surprising, since it had been hoped that it would be possible to exploit the vascular-destructive mode of action of BPD-MA to enhance the PDT effect.

Thus the present invention pertains to the combined use of EtNBS with a promising new photosensitizer known as benzoporphyrin derivative monoacid ring A (BPD-MA) in an attempt to enhance PDT efficacy. As stated above, EtNBS appears to eradicate tumors primarily by direct tumor cell killing with minimal effects to the vasculature. Conversely, the work of Richter et al., *Br. J. Cancer* 63:87–93, (1991), showed that BPD-MA appears to primarily destroy solid tumors indirectly by the rapid occlusion of the microvasculature and the ensuing hypoxia. BPD-MA was used because it is activated by a wavelength of light (690 nm) that penetrates tissue to a greater depth than Photofrin™ (630 nm) and has been reported to be considerably more phototoxic to cancer cells in vitro (Richter, A. M., et al., *JNCI* 79:1327–1332, 1987). Also, the pharmacokinetics of drug uptake by the tumor is similar to EtNBS, i.e. parenteral administration results in the rapid accumulation of BPD-MA in the tumor. In addition, it is retained in the skin for a significantly shorter period of time compared to Photofrin™. The surprisingly enhanced PDT effect of the combination of EtNBS and BPD-MA over either chromophore alone is illustrated by the treatment of large tumors (8–10 mm), which have been shown in preliminary investigations not to respond well to phototherapy with either chromophore alone (Cincotta, L., et al., *Cancer Res.* 54:1249–1258, 1994; Cincotta, L., et al. *Photochem. Photobiol.* 46:751–758, 1987).

The method of the present invention, treatment of mammals with the photosensitizer combination of EtNBS and BPD-MA and light, is the first to demonstrate a consistent eradication of large (8–10 mm) murine tumors with PDT. As indicated above, it is generally acknowledged in the art that PDT with a variety of photosensitizers is ineffective in eradicating tumors in mouse model systems once the diameter increases above 5–7 mm. Not only is the effect of the instantly claimed combination treatment much more dramatic than the result obtained from doubling the light dose or the concentration of either photosensitizer alone (implying a synergistic rather than additive effect); it was found that a higher BPD-MA dose (5.0 mg/kg) resulted in the significant death (77%) of animals treated with PDT. Therefore, in the animal model, the combined therapy of the present invention also increases the therapeutic index of phototreatment dramatically (i.e. there were zero deaths). The phenomenon of acute toxicity in animals with other modes of PDT has been reported previously (Dougherty, T. J., *Photochem. Photobiol.* 45:879–889, 1987; Cincotta, L., et al., *Cancer Res.* 54:1249–1258, 1994; Ferrario, A., et al., *Cancer Res.* 50:539–543, 1990).

Thus, it has now been surprisingly and unexpectedly discovered that the growth arrest or eradication of tumors that can be achieved by using only EtNBS as the PDT agent can be significantly augmented by simultaneously administering the PDT agent BPD-MA. It has been discovered that the effect of combining these two photosensitizers is synergistic rather than additive, allowing lower doses of each chromophore to be used and improving the therapeutic index of the chromophores. No damage to photoirradiated skin is found when dosages effective for tumor killing are used.

This discovery was entirely unexpected because the mechanism of action of tumor eradication using the combination of dyes is inconsistent with the known mechanisms of action of BPD-MA by itself, which is occlusion of tumor vasculature and subsequent tumor hypoxia. Nothing in the prior art suggested that the use of BPD-MA with EtNBS would increase the tumor cell killing effect associated with EtNBS while negating the vasculature-occluding effects previously associated with BPD-MA.

SUMMARY OF THE INVENTION

Thus, one aspect of the present invention is a method for treating solid tumors of all types in a subject which comprises administering to a subject a therapeutically effective amount of a first chromophore and a therapeutically effective amount of a second chromophore, exposing the tumor to broad spectrum light at a predetermined time after administration of said chromophores, said broad spectrum light comprising light of a first wavelength predetermined to be absorbed by the first chromophore and light of a second wavelength predetermined to be absorbed by the second chromophore. Alternatively, after administration of chromophores the tumor can be exposed, after specific time intervals, to light of specific wavelengths, e.g. using a tunable laser, predetermined to be absorbed by the first chromophore and the second chromophore.

Another aspect of the present invention is a method for eradicating or reducing the size of solid tumors which comprises contacting the tumor with effective amounts of a first chromophore and a second chromophore followed at the appropriate time interval by exposure of the tumor to broad spectrum light which comprises light of a first wavelength predetermined to be absorbed by the first chromophore and light of a second wavelength predetermined to be absorbed by the second chromophore. Alternatively, after administration of chromophores the tumor can be exposed, after specific time intervals, to light of specific wavelengths, e.g. using a tunable laser, redetermined to be absorbed by the first chromophore and the second chromophore.

The advantages of the present invention include:
  enhanced reduction in tumor growth and accelerated eradication of tumor issue.
  the ability to inhibit or eradicate tumors without the debilitative effects of chemotherapeutic agents or ionizing radiation.

Other features and advantages of the present invention will be apparent from the following description taken in conjunction with the accompanying drawings.

DETAILED DESCRIPTION OF THE INVENTION

All references, patents, and patent applications referred to in this disclosure are hereby incorporated by reference in their entirety.

Preparation of the Chromophores

The preferred benzophenoxazine analog chromophores for use in the present invention and the synthesis of the benzophenoxazine analog chromophores are those described in Foley et al., U.S Pat. No. 4,962,197, which is herein incorporated by reference. The photosensitizer can be purified by medium pressure (100 psi) liquid chromatography using silica gel (Woelm 32–63) as a solid phase and eluting with a linear gradient of methylene chloride:methanol (100:0–90:10). The resulting purified photosensitizer is homogeneous by thin layer chromatography and high field nuclear magnetic resonance spectroscopy (JEOL 400 MHz). Aqueous solutions of the compound can be prepared in isotonic sucrose at a concentration of 0.175 mg/ml.

BPD-MA can be made by methods described in Levy et al., U.S. Pat. No. 4,920,143 and Pangka, V. S. et al., *J. Org. Chem.* 51:1094–1100, (1986), both of which are herein incorporated by reference. The method comprises preparing protoporphyrin IX dimethyl ester from hematoporphyrin (Sigma Chemical Co., St. Louis, Mo.) and refluxing the protoporphyrin IX dimethyl ester with dimethyl acetylene dicarboxylate in an organic solvent, in the dark, for 3 to 6 days to give Diels-Alder adducts. The Diels-Alder adducts are chromatographed on silica gel in dichloromethane/2% methanol. The products are rearranged with 1.5-diazabicyclo[5.4.0]undec-5-ene. The resulting diastereomeric mixture of methyl esters is hydrolyzed with 25% hydrochloric acid at room temperature for 5 hours in the dark. The mono- and di-acid compounds are separated by methods well-known in the art. BPD-MA can also be obtained from Quadra Logic Technologies Inc. (Vancouver, BC, Canada) and can be used without further purification. The lipophilic nature of BPD-MA presents a problem for in vivo drug delivery. Therefore, working lipoprotein solutions should be prepared immediately before use by incubating 0.25 mg of BPD-MA stock solution with 0.25 mg of human LDL (Sigma) in a total volume of 1 ml PBS at 37° C. for 30 min. Lipoprotein formulation of BPD-MA can deliver larger quantities of drug to tumors without changing the characteristic pattern of BPD-MA distribution in tissues.

Photophysical Properties

Figure 1A:
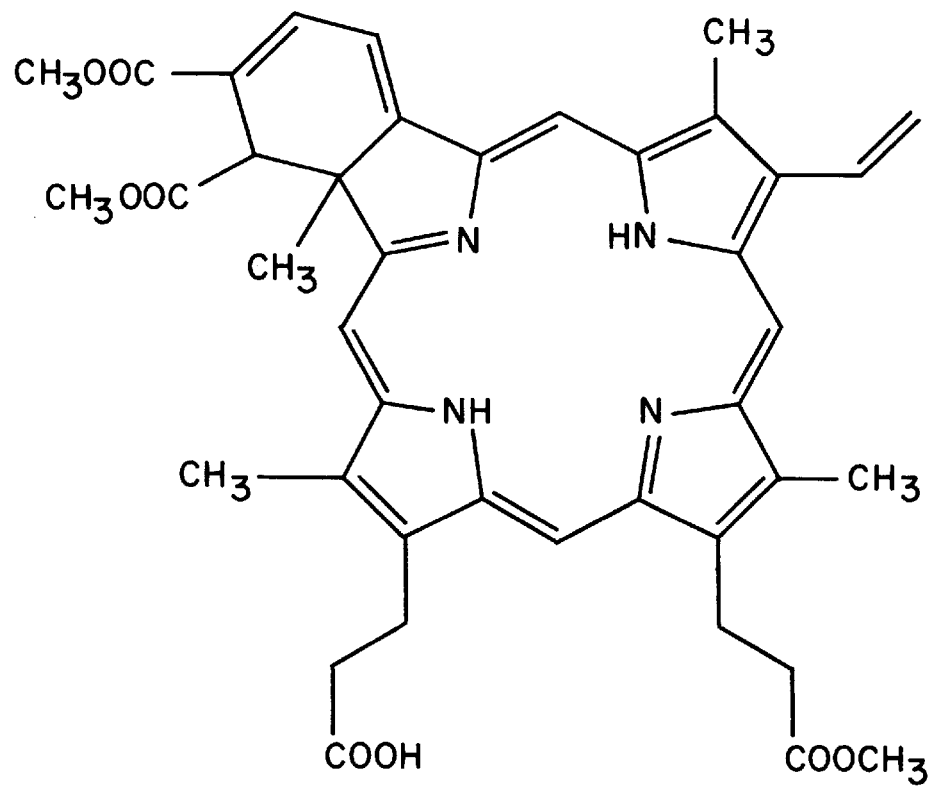
FIG. 1A. shows the chemical structure of BPD-MA (one regioisomer)
Figure 1B:
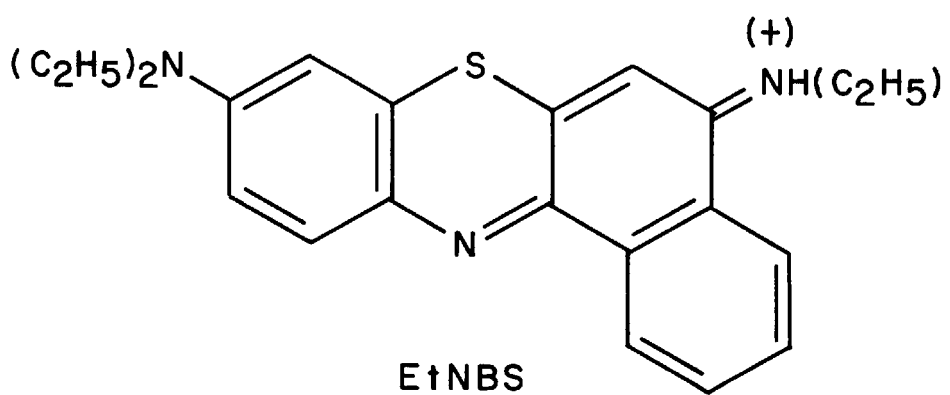
FIG. 1B shows the chemical structure of EtNBS.
Figure 2:
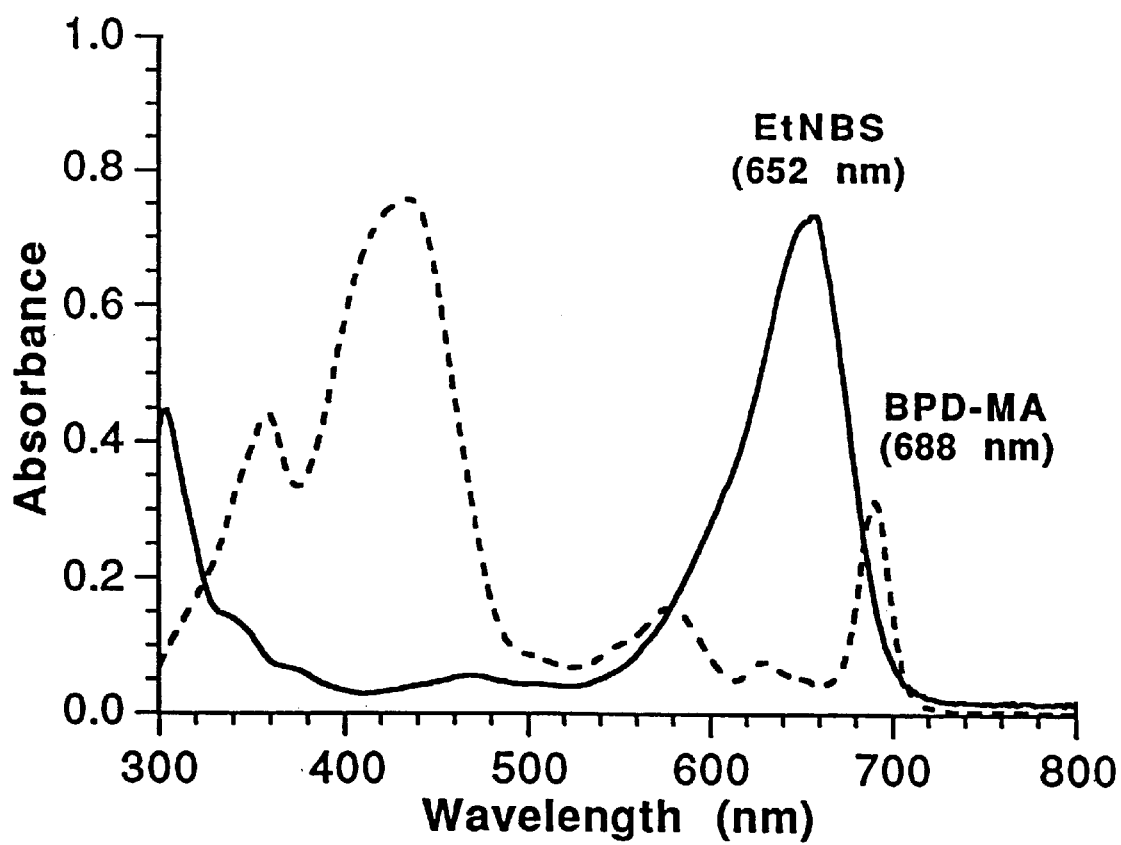
FIG. 2. Absorption spectra of $1\times10^{-5}$ M EtNBS and BPD-MA in Methanol.

The molecular structures of the EtNBS, a preferred benzophenoxazine analog, and BPD-MA are shown in FIG. 1. Their absorption spectra in methanol, presented for comparative purposes in FIG. 2, show very little overlap at the wavelengths of photoirradiation (i.e. 652 nm and 690 mn). It should be understood that the absorption spectra in methanol might not be the same in tumor tissue or cells since it is known that both drugs undergo shifts in their visible spectra upon going from organic to aqueous solvents. In particular, the absorption spectrum of EtNBS becomes broader in cells due to dimer formation. The fluorescence quantum yield ($\Phi f$) for BPD-MA and EtNBS (data not shown) were determined in methanol to be 5% and 15%, respectively, while their singlet oxygen yields are 76% and 2.5%, respectively. BPD-MA is reported in the literature to be very photostable in a variety of organic solvents with photobleaching quantum yields in the order of $5\times10^{-5}$. However, it has been noted during fluorescence microscopy of EMT-6 cells both in culture and in tumor tissue that BPD-MA is very rapidly photobleached following excitation in the Soret band. Contrariwise, EtNBS is relatively stable to the conditions used during the fluorescence experiment. Additional detailed information concerning the physical and photophysical characteristics can be found in Cincotta et al., *Cancer Res.* 54:1249–1258, (1994); and Aveline et al., *Photochem. Photobiol.* 59:328–335, (1994) hereby incorporated by reference.

Chromophore Dosage Forms and Administration

The benzophenoxazine analog chromophore is preferably a benzophenothiazine or pharmaceutically acceptable salt thereof. Most preferably, the chromophore is 5-ethylamino-9-diethylamino-benzo[a]phenothiazinium chloride (EtNBS).

The benzophenoxazine analog chromophore is typically dissolved in sterile isotonic sucrose or saline at 0.1 to 1.0 mg/ml, and preferably 0.25 mg/ml. Administration can be via an intravenous or subcutaneous route, in a suitable carrier vehicle which facilitates tissue uptake.

Administration of benzophenoxazine analog chromophore is generally such that between about 0.05 and about 10 mg/kg of body weight of chromophore is delivered to the patient, preferably between about 0.1 and about 5 mg/kg of body weight, and most preferably between about 0.5 and about 5 mg/kg of body weight. The active agent is preferably administered by infusion at between 0.25 and 0.5 ml per minute. Benzophenoxazine analog chromophores are preferably administered from about 0.5 to about 5 hours before irradiation with light, depending on the benzophenoxazine analog's route of administration, as will be elaborated below.

The BPD-MA chromophore should be incubated with an equal weight of human LDL in phosphate buffered saline before administration in order to improve solubility in body fluids. Typically, each 0.25 mg of both LDL and BPD-MA is dissolved in 1 ml of phosphate buffered saline. The BPD-MA chromophore can be administered intravenously or intraperitoneally.

Administration of BPD-MA is generally such that between about 0.05 and 10 mg/kg of body weight is delivered to the patient, preferably between about 0.1 and 5 mg/kg of body weight, and most preferably between about 0.5 and 5 mg/kg of body weight. BPD-MA is preferably administered from about 0.5 to about 12 hours before irradiation with light, depending on the route of BPD-MA administration, as will be elaborated below.

Light Activation of Administered Chromophores

Light-induced killing of solid tumors according to the invention can be carried out on any solid tumors which are accessible to light from conventional sources (e.g. a xenon arc lamp, an incandescent white light) or from a laser. If a tumor is on the body surface any light source can be employed that provides light at the appropriate wavelengths to activate the dyes (i.e. 652 mn and 690 nm) and that can deliver 50 to 200 mW per square centimeter of treated area. It is preferred to use a tunable argon-dye laser (e.g. a 5 watt argon ion pumped tunable dye laser, Coherent, model Innova 100, Palo Alto, Calif.) using DCM (Exiton Chemical Co., Dayton, Ohio). Similar lasers are also commercially available from, for example, Spectra Physics, Mountain View, Calif. However, a projector light source may also be employed. For tumors within the body, which are inaccessible to direct light sources, light is administered via optical fibers and the light source is a laser.

Preferably a time interval passes between administration of chromophores and irradiation (i.e. exposure) of the tumor to light in order to give the chromophores time to reach the target tissues and to preferentially dissipate from normal cells, enhancing the differential chromophore concentration in tumor cells compared to normal cells. This time interval varies depending on the chromophore administered and the route of administration. When a benzophenoxazine analog such as EtNBS is administered intravenously, the time interval is from between 0.5 and 5 hours, and preferably about 1 hour. When a benzophenoxazine analog such as EtNBS is administered subcutaneously, the time interval is between about 0.5 and 5 hours, and preferably about 3 hours. When BPD-MA is administered intravenously, the time interval is between about 0.5 and 5 hours, and preferably about 1 hour. When BPD-MA is administered intraperitoneally, the time interval is between about 5 and about 12 hours, and is preferably about 8 hours.

Thus, administration of the benzophenoxazine analog and BPD-MA chromophores must be carefully timed so that subsequent light irradiation will take place when both dyes have achieved their maximal concentration in tumor tissue relative to their concentration in normal tissues. For example, if BPD-MA and benzophenoxazine analog chromophores are both administered intravenously, they can be administered simultaneously and, optionally, in the same infusion. However, if the modes of administration are mixed, for example, if BPD-MA is given intraperitoneally and benzophenoxazine analog is given intravenously, BPD-MA must be administered about 7 hours prior to intravenous administration of benzophenoxazine analog (to enable irradiation of both chromophores at the same time).

The light to which the tumor is exposed can be broadband white light containing wavelengths of between 600 and 900 nm. The light source must include light at 652 nm and 690 nm to be useful in the present invention. When a broad-spectrum light source is used, the irradiation at 652 nm and 690 nm can be concomitant. Preferably, the tumor is exposed to light of two specific wavelengths, 652 nm and 690 nm. Using filters, the broadband light can be narrowed to the specific wavelengths of 652 nm and 690 nm, and exposure to the different wavelengths can be sequential, preferably first to 652 nm light and then to 690 nm light. When a laser is used, the tumor is first exposed to 652 nm light and then immediately following is exposed to 690 nm light.

The total light energy delivered at each wavelength is between about 50 and about 200 Joules/cm$^2$, preferably about 100 Joules/cm$^2$. The power density of the light is preferably between about 50 and about 200 mWatts/cm$^2$, and is most preferably about 50 mWatts/cm$^2$. Delivery of laser light is carried out according to the well-known methods currently used for HPD-mediated laser therapy (Foultier et al., *J. Photochem. Photobiol. B. Biol.* 10:119–132, 1991). The output beam from the dye laser can be coupled to a 400 $\mu$m quartz fiberoptic cable fitted with a microlens to ensure an even light distribution throughout the treatment field. The wavelength is tuned with a birefringent filter and the power density should be adjusted for a spot size to encompass the tumor and a margin of some normal tissue.

EXAMPLE 1

Treatment of Tumors with Combination BPD/EtNBS Phototherapy

The well-known EMT-6 tumor cell line, a mildly immunogenic, murine mammary sarcoma syngeneic to BALB/C mice maintained according to the protocol of Rockwell et al., *JNCI* 49:735–749, (1972) was obtained. The cells are cultured in RPMI 1640 (Sigma Chemical Co., St. Louis, Mo.) supplemented with 10% fetal bovine serum from Sigma, 105 units/liter penicillin, 100 mg/liter streptomycin, 25 mM sodium bicarbonate and 3.5 ml of 2-mercaptoethanol (Sigma). The cells are incubated at 37° C. in a humidified 95% air:5% $CO_2$ atmosphere.

Male BALB/C mice (6–8 weeks of age) can be obtained from Charles River Breeding Laboratories, Wilmington, Mass. The mice are acclimated to the 12:12 hour light:dark cycle of an animal care facility for at least 1 week prior to inoculation with tumor cells and should weigh 20–25 g at the time of PDT treatment. After depilation, mice are inoculated in the right flank with $1.7 \times 10^6$ EMT-6 cells suspended in 0.1 ml of media. Mice are photoirradiated when the tumor surface diameter reached 8–10 mm and a thickness of 3–5 mm (8–12 days). For comparative purposes, these tumors have volumes of 200–400 mm$^3$ ($V=0.4 \times L \times W^2$ where L is the long axis and W is the short axis).

Mice receiving EtNBS were given a subcutaneous injection at the scruff of the neck 3 hours prior to phototherapy and unless otherwise noted were given a fluence of 100 J/cm$^2$ of 652 nm light at a fluence rate of 50 mW/cm$^2$. Mice receiving BPD-MA were given an intraperitoneal injection 6 hours prior to phototherapy with 100 J/cm$^2$ of 690 nm light at a fluence rate of 150 mW/cm$^2$. The mice were divided into eight different treatment groups as follows: 1) no photosensitizers and no light, 2) 2.5 mg BPD-MA/kg body weight (BW) and 5.25 mg EtNBS/kg BW; no light, 3) 5.25 mg EtNBS/kg BW+light, 4) 2.5 mg BPD-MA/kg BW+light, 5) 10.5 mg EtNBS/kg BW+200 J/cm$^2$, 6) 5.0 mg BPD-MA/kg BW+light, 7) a combination of 5.25 mg EtNBS/kg BW and 2.5 mg BPD-MA/kg BW; treated first with 652 nm light followed by 690 nm light and 8) similar to group 7 but the exposure to the two wavelengths of light were in the reverse order (i.e. 690 nm followed by 652 nm light). Tumor exposures to light were carried out on immobilized animals without anesthesia via a 5 W argon ion pumped tunable dye laser (Coherent, model Innova 100, Palo Alto, Calif.) using DCM (Exiton Chemical Co., Dayton, Ohio). The output beam from the dye laser was coupled to a 400 $\mu$m quartz fiberoptic cable fitted with a microlens to ensure an even light distribution throughout the treatment field. The wavelength was tuned with a birefringent filter and the power density was adjusted for a spot size of 1.2 cm which encompassed the tumor as well as some normal tissue. Temperature measurements before and during light treatment were monitored by means of a microthermocouple (model 852820, Cole Parmer, Chicago, Ill.) placed on the surface of the tumor.

Mice bearing tumors were examined daily for the first 14 days post-PDT. The inhibition of tumor growth compared to controls or the disappearance of palpable tumor during this time period was considered a positive response. Mice were sacrificed at 14 days and the tumor mass was removed, separated from overlying skin and weighed.

Mice were sacrificed by cervical dislocation 24 hours following light treatment and the entire light treated area including the tumor, surrounding skin, and underlying musculature was removed and fixed in phosphate buffered formalin. The fixed tissue was embedded in paraffin, sectioned at either 5 or 10 $\mu$m intervals, stained with hematoxylin and eosin and examined with light microscopy.

Figure 3:
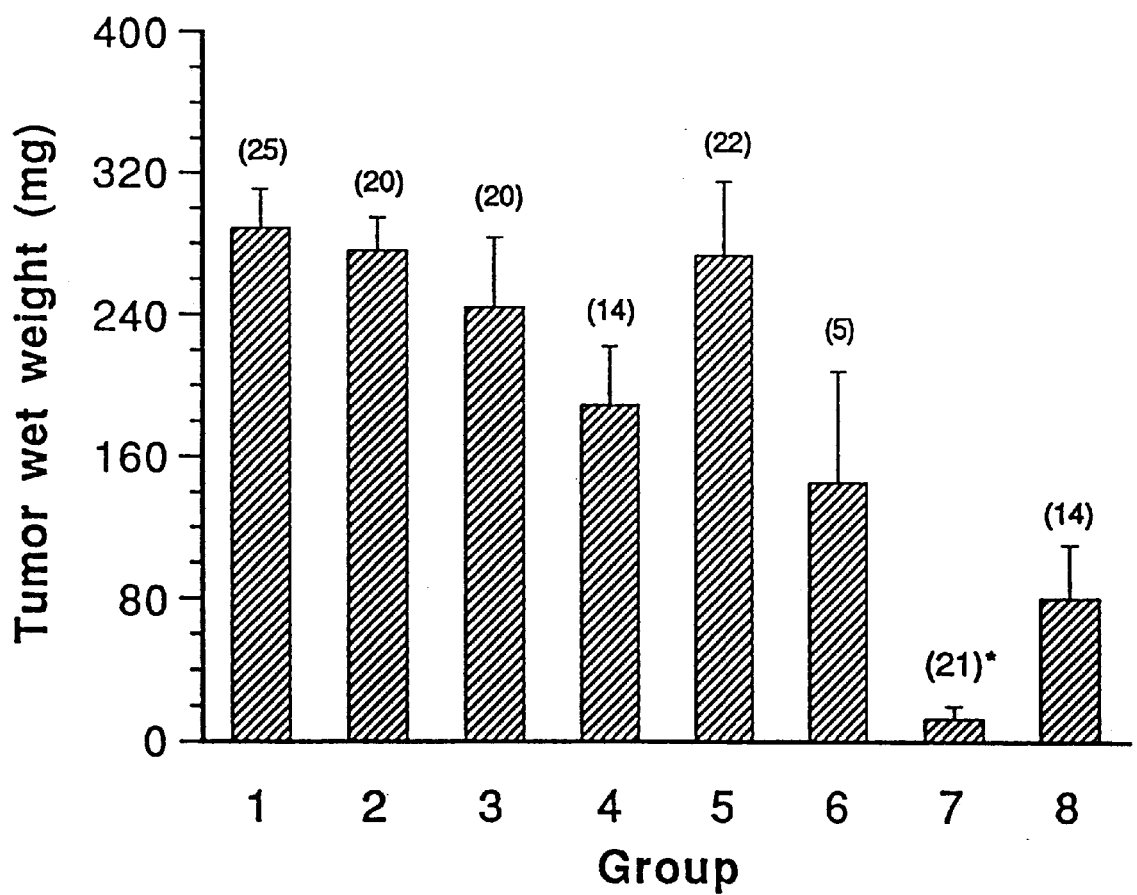
FIG. 3. Tumor wet weights 2 weeks post-PDT with EtNBS and BPD-MA.
Figure 4:
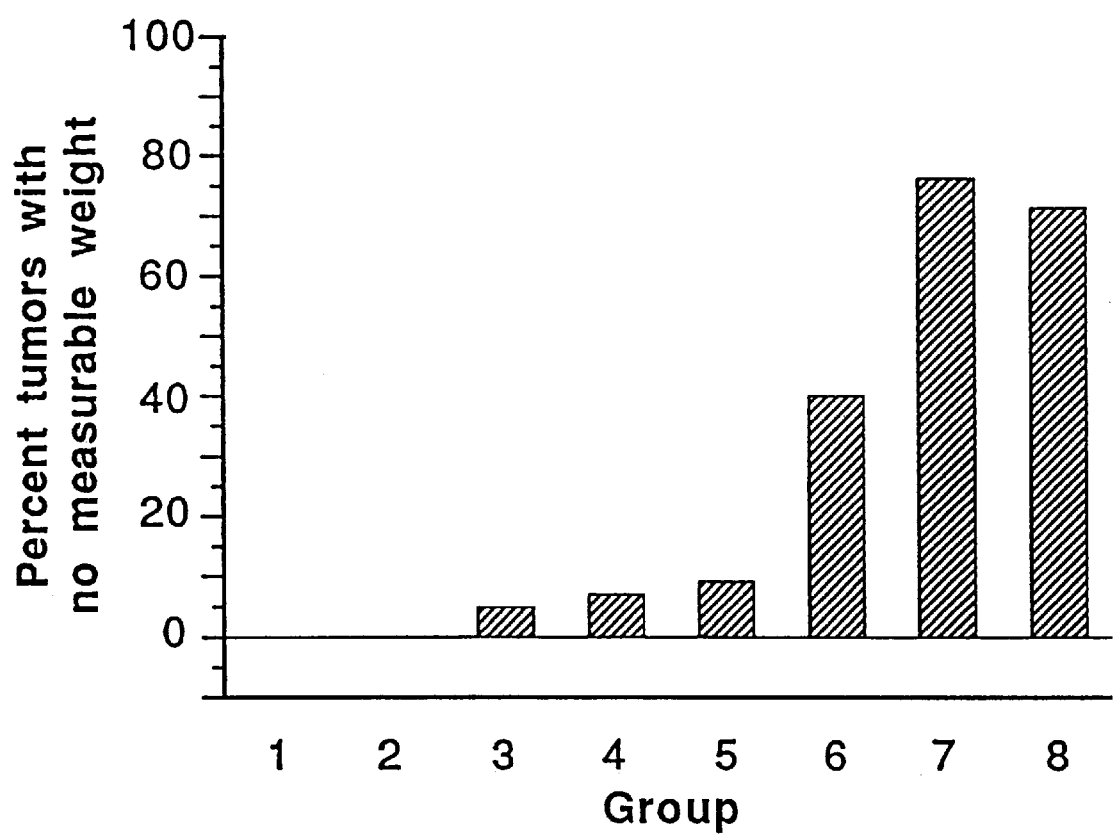
FIG. 4. Percent tumors with no measurable weight 2 weeks post-combination PDT. Groups are the same as in FIG. 3.

The photochemotherapeutic effects of BPD-MA or EtNBS alone or in combination are summarized in FIG. 3 and 4. The tumor wet weights (+/SEM) for each group of mice are as follows: 1) 289±22, 2) 276±19, 3) 244±39, 4) 189±33, 5) 273±19, 6) 145±63, 7) 13±7 and 8) 80±30. There were no cases of tumor regression in control groups 1 and 2 (n=45). Mice given either 5.25 mg/kg EtNBS (group 3) or 2.5 mg/kg BPD-MA (group 4) and then photoirradiated with the appropriate light source showed no statistically significant (Student's t test) reduction in tumor weight compared to the controls. However, 5% and 7% of the tumors in these groups, respectively, were non-measurable at 2 weeks post-PDT.

In group 5, where the mice received double the concentration of EtNBS (10.5 mg/kg) and light (200 J/cm$^2$), there was also no statistical change in average tumor weight at the end of the observation period. However, there was an increase in the number of tumor free mice (9%). Although there was an inflammatory response (slight to moderate edema) with some tumors showing eschar formation in this group, the degree of necrosis must not have been substantial in relation to the tumor size since the majority of these tumors subsequently grew as rapidly as tumors in the untreated group.

Preliminary experiments with double the concentration of BPD-MA (5.0 mg/kg) indicated that the mice could not survive a light dose of 200 J/cm$^2$. Therefore, mice in group 6 were given 5.0 mg/kg BPD-MA and a dose of only 100 J/cm$^2$. Even under these conditions, 77% of the mice died within 48 hours of receiving PDT. However, 2 of the 5 mice which did survive the treatment were tumor free at 2 weeks post-PDT.

The animals that received the combination drug regimens (groups 7 and 8) had a dramatic response to PDT (P<0.01 vs. control groups 1 and 2). This was especially true for group 7 which was photoirradiated with 100 J/cm$^2$ of 652 nm light prior to photoirradiation with 100 J/cm$^2$ of 690 mn light. The locus of light exposure developed moderate edema 2–3 hours following PDT which persisted for 24–72 hours but there was no sign of erythema. There were signs of hemorrhage within some tumors, but it did not appear prominent. While the degree of eschar formation varied from tumor to tumor, it only occurred directly over the tumor (36–48 hours post-PDT) as opposed to the entire phototreated area; the normal skin surrounding the tumor was unaffected. In tumors that regressed, the tumor mass became non-palpable within 7–10 days and the scab eventually fell off leaving healed skin with hair. Of the photoirradiated tumors in group 7 and 8, 76 and 71% respectively, were non-measurable (i.e. not visible upon resection) two weeks post-PDT.

Figure 5A:
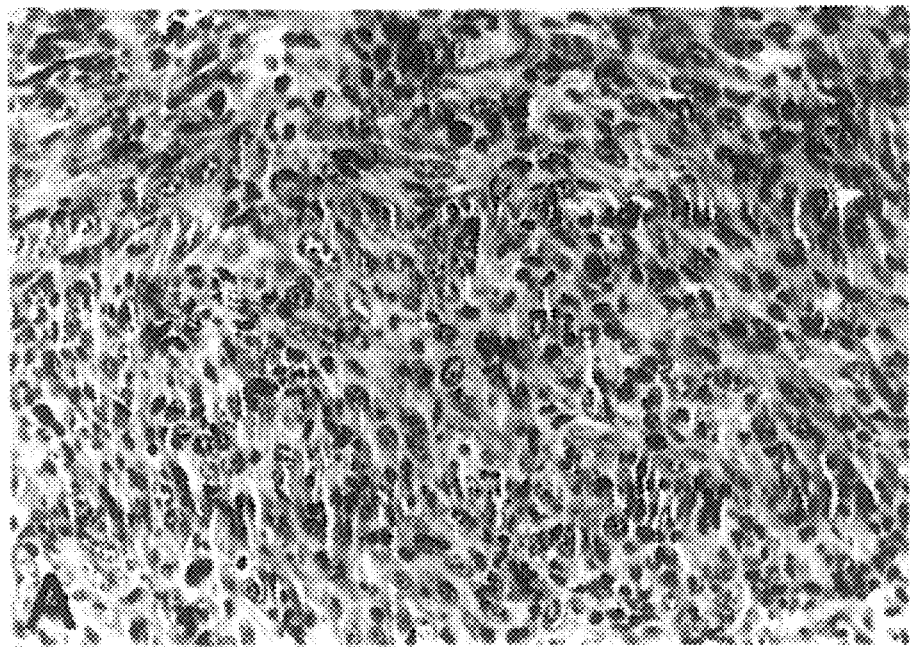
FIG. 5a. 24 h Post-phototreatment photomicrographs of EMT-6 tumors exposed to 5.25 mg of photoinactive analog EtNBA (×350).
Figure 5B:
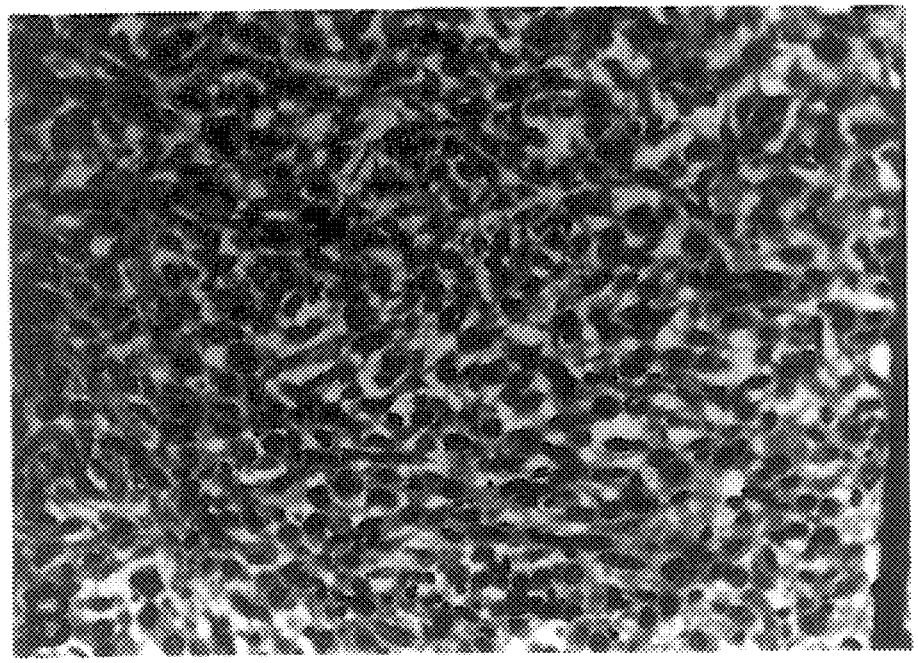
FIG. 5b. 24 h Post-phototreatment photomicrographs of EMT-6 tumors exposed to 5.25 mg of EtNBS (×350).
Figure 5C:
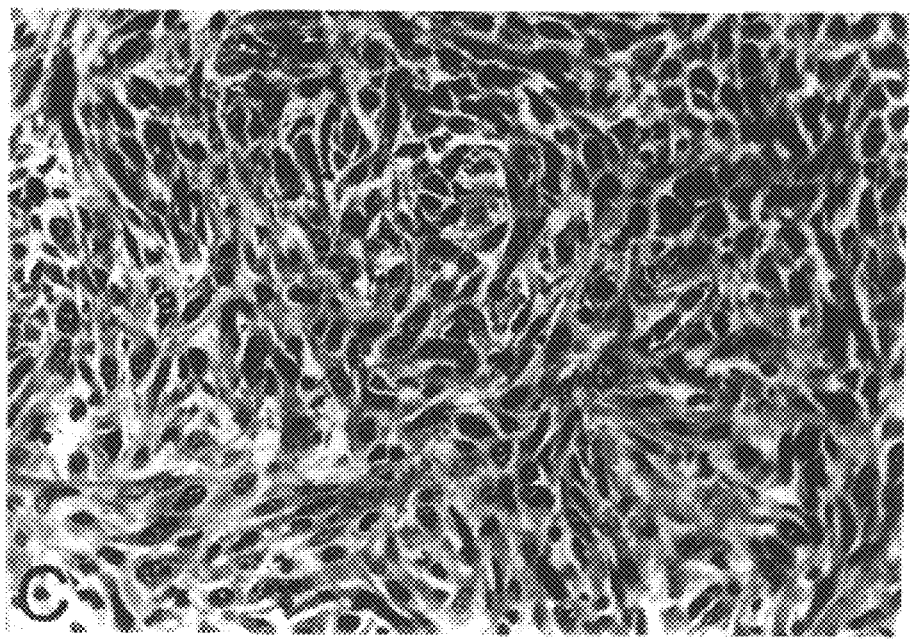
FIG. 5c. 24 h Post-phototreatment photomicrographs of EMT-6 tumors exposed to 2.5 mg of BPD-MA (×350).
Figure 5D:
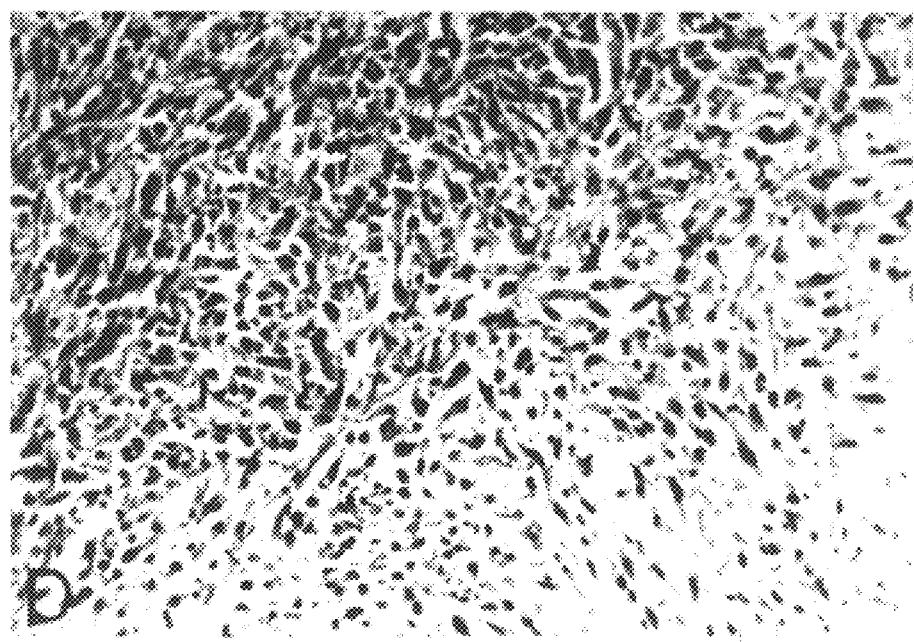
FIG. 5d. 24 h Post-phototreatment photomicrographs of EMT-6 tumors exposed to 2.5 mg of BPD-MA and 5.25 mg of EtNBS (×350).

Histological examination (24 hours post-PDT) of the center of tumors treated as in groups 3 and 4 are shown in FIG. 5b and 5c, respectively. There was minimal phototoxicity associated with the individual drugs at the dosages used. Contrariwise, when the two drugs were used at the same concentration but in combination, as in group 7 (FIG. 5d) there was nearly complete destruction of the tumor mass with little to no damage to the blood vasculature and no extravasation of red blood cells. Any viable cells present tended to be localized to the bottom (distal to light source) of the tumor mass. In contrast to the prominent destruction of the tumor, the skin surrounding the tumor displayed near normal histology. A photoinactive analog (EtNBA) of EtNBS was used as a control to differentiate photoinduced thermal effects from photodynamic effects. When EMT-6 tumor bearing mice were injected with 10.5 mg/kg of EtNBA and photoirradiated 3 hours later with fluences and light doses ranging from 50–150 mW/cm$^2$ and 100–200 J/cm$^2$, respectively, no phototoxic effects are observable (FIG. 5a). This indicates that photodynamic and not photothermal phenomena are responsible for the phototoxic effects following EtNBS/PDT.

The results obtained using PDT when tumors containing both photosensitizers are first photoirradiated with 690 nm light followed by 652 nm light (FIG. 4, group 8) appear to verify the histological data suggesting that there are minimal vascular effects at the BPD-MA dose used (2.5 mg/kg) in the combination therapy, since the number of mice that were tumor free following this reversed phototreatment only decreased from 76% to 71%.

If there were substantial vascular occlusion with BPD-MA, as reported by others, one would expect a substantial decrease in the PDT response, because the resulting oxygen deprivation should prevent subsequent EtNBS, oxygen dependent, photochemistry from occurring. Thus, the results of the combination therapy of the present invention, (i.e. little or no vascular occlusion with significant PDT response) are surprising and unexpected in light of the teachings of the prior art. The results above also illustrate the surprising efficacy of the combination therapy, as compared with prior art PDT regimens.

What is claimed is:

1. A method for treating a mammal bearing one or more solid tumors comprising the steps of:

contacting the cells of said tumor with a first chromophore and a second chromophore; and exposing said contacted tumor cells to light of a first predetermined wavelength and power density and energy level and light of a second predetermined wavelength and power density and energy level;

wherein said first chromophore is selected from the group consisting of benzophenoxazine analogs, and pharmaceutically acceptable salts thereof and said second chromophore is BPD-MA.

2. A method for treating a mammal bearing one or more solid tumors comprising the steps of:

administering to said mammal phototoxically effective amounts of a first chromophore and a second chromophore; and exposing said tumor to light of a first predetermined wavelength and power density and energy level and light of a second predetermined wavelength and power density and energy level;

wherein said first chromophore is selected from the group consisting of benzophenoxazine analogs, and pharmaceutically acceptable salts thereof and said second chromophore is BPD-MA.

3. The method of claim 1 wherein said first chromophore is administered intravenously or subcutaneously and said second chromophore is administered intravenously or intraperitoneally.

4. The method of claim 2 wherein said first chromophore is administered intravenously or subcutaneously and said second chromophore is administered intravenously or intraperitoneally.

5. The method of claim 3 wherein said effective amount of said first chromophore and said second chromophore is between about 0.05 and 10 mg/kg of body weight.

6. The method of claim 4 wherein said effective amount of said first chromophore and said second chromophore is between about 0.05 and 10 mg/kg of body weight.

7. The method of claim 5 wherein said effective amount of said first chromophore and said second chromophore is between about 0.1 and 5 mg/kg of body weight.

8. The method of claim 6 wherein said effective amount of said first chromophore and said second chromophore is between about 0.1 and 5 mg/kg of body weight.

9. The method of claim 7 wherein:

the energy level of said light of said first predetermined wavelength is between about 50 and 200 Joules/cm$^2$;

the energy level of said light of said second predetermined wavelength is between about 50 and 100 Joules/cm$^2$ the power density of said light is between about 50 and 200 mWatts/cm$^2$;

said tumor is exposed to said light between about 0.5 and 8 hours after administration of said first and said second chromophores.

10. The method of claim 8 wherein:

the energy level of said light of said first predetermined wavelength is between about 50 and 200 Joules/cm$^2$;

the energy level of said light of said second predetermined wavelength is between about 50 and 100 Joules/cm$^2$ the power density of said light is between about 50 and 200 mWatts/cm$^2$;

said tumor exposed to said light between about 0.5 and 8 hours after administration of said first and said second chromophores.

11. A method of claim 9 wherein said first chromophore is a benzophenothiazine or a pharmaceutically acceptable salt thereof.

12. A method of claim 10 wherein said first chromophore is a benzophenothiazine or a pharmaceutically acceptable salt thereof.

13. The method of claim 11 wherein said benzophenothiazine is 5-ethylamino-9-diethylamino-benzo[a]phenothiazinium chloride.

14. The method of claim 12 wherein said benzophenothiazine is 5-ethylamino-9-diethylamino-benzo[a]phenothiazinium chloride.

15. The method of claim 13 wherein:

the energy level of said light of said first and said second predetermined wavelengths is about 100 Joules/cm$^2$;

the power density of said light is about 50 mWatts/cm$^2$;

said tumor is exposed to said light at about 3 hours after administration of said first and second chromophores;

said first chromophore is 5-ethylamino-9-diethylaminobenzo[a]phenothiazinium chloride; and said first chromophore is administered in an amount between about 0.5 and 5 mg/kg of body weight.

16. The method of claim 14 wherein:

the energy level of said light of said first and said second predetermined wavelengths is about 100 Joules/cm$^2$;

the power density of said light is about 50 mWatts/cm$^2$;

said tumor is exposed to said light at about 3 hours after administration of said first and second chromophores;

said first chromophore is 5-ethylamino-9-diethylaminobenzo phenothiazinium chloride; and said first chromophore is administered in an amount between about 0.5 and 5 mg/kg of body weight.

17. The method of claim 15 wherein said first chromophore and said second chromophore are administered intravenously and said tumor is exposed to said light between about 1 hour after administration of said first chromophore and said second chromophores.

18. The method of claim 16 wherein said first chromophore is administered subcutaneously, said second chromophore is administered intraperitoneally five hours prior to said administration of said first chromophore, and said tumor is exposed to said light about 3 hours after administration of said first chromophore.

* * * * *